United States Patent
Yokoyama et al.

(10) Patent No.: US 10,434,459 B2
(45) Date of Patent: Oct. 8, 2019

(54) METHOD AND DEVICE FOR TREATING NITROSO COMPOUND

(71) Applicant: MITSUBISHI HITACHI POWER SYSTEMS, LTD., Yokohama-shi, Kanagawa (JP)

(72) Inventors: Koichi Yokoyama, Yokohama (JP); Eiji Miyamoto, Yokohama (JP); Jun Shimamura, Yokohama (JP)

(73) Assignee: MITSUBISHI HITACHI POWER SYSTEMS, LTD., Kanagawa (JP)

(*) Notice: Subject to any disclaimer, the term of this patent is extended or adjusted under 35 U.S.C. 154(b) by 126 days.

(21) Appl. No.: 15/541,934

(22) PCT Filed: Jan. 7, 2015

(86) PCT No.: PCT/JP2015/050280
§ 371 (c)(1),
(2) Date: Jul. 6, 2017

(87) PCT Pub. No.: WO2016/110965
PCT Pub. Date: Jul. 14, 2016

(65) Prior Publication Data
US 2018/0001252 A1    Jan. 4, 2018

(51) Int. Cl.
*B01D 53/14* (2006.01)
*B01D 53/62* (2006.01)
(Continued)

(52) U.S. Cl.
CPC ....... *B01D 53/1418* (2013.01); *B01D 53/005* (2013.01); *B01D 53/145* (2013.01);
(Continued)

(58) Field of Classification Search
None
See application file for complete search history.

(56) References Cited

U.S. PATENT DOCUMENTS 3,429,924 A * 2/1969 Morgana ............... C07C 209/68
564/410
4,226,789 A * 10/1980 Eizember ............. C07C 209/84
564/112
(Continued)

FOREIGN PATENT DOCUMENTS

JP    54-022329 A    2/1979
JP    62-292618 A    12/1987
(Continued)

OTHER PUBLICATIONS

Notification of Reasons for Refusal dated Apr. 27, 2018, issued in counterpart Japanese application No. 2016-568211, with English translation. (11 pages).
(Continued)

*Primary Examiner* — Tam M Nguyen
(74) *Attorney, Agent, or Firm* — Westerman, Hattori, Daniels & Adrian, LLP

(57) ABSTRACT

A method for decomposing a nitroso compound, comprising: adding an aqueous solution containing hydrogen halide to a liquid to be treated that contains the nitroso compound in such a manner that the hydrogen halide is present in an amount of 2 mol or more and 20 mol or less per mol of a nitroso group in the nitroso compound; and subsequently heating the resulting liquid to be treated at a temperature of not lower that 75° C. and not higher than a boiling point of water under ordinary pressure, thereby an amines are recovered.

6 Claims, 3 Drawing Sheets

(51) Int. Cl.
*C01B 32/50* (2017.01)
*B01D 53/00* (2006.01)
*C07C 209/38* (2006.01)

(52) U.S. Cl.
CPC ......... *B01D 53/1425* (2013.01); *B01D 53/62* (2013.01); *C01B 32/50* (2017.08); *C07C 209/38* (2013.01); *B01D 53/1475* (2013.01); *B01D 2251/50* (2013.01); *B01D 2251/502* (2013.01); *B01D 2251/604* (2013.01); *B01D 2252/204* (2013.01); *B01D 2258/0283* (2013.01); *Y02C 10/06* (2013.01)

(56) References Cited

U.S. PATENT DOCUMENTS

| | | |
|---|---|---|
| 2004/0253159 A1 | 12/2004 | Hakka et al. |
| 2011/0135550 A1 | 6/2011 | Nagayasu et al. |
| 2011/0308389 A1 | 12/2011 | Graff et al. |
| 2012/0125196 A1 | 5/2012 | Woodhouse et al. |
| 2013/0313475 A1 | 11/2013 | Fischer et al. |
| 2013/0315809 A1 | 11/2013 | Shimamura |
| 2014/0345458 A1 | 11/2014 | Klinker |

FOREIGN PATENT DOCUMENTS

| | | |
|---|---|---|
| JP | 8-89756 A | 4/1996 |
| JP | 2006-527153 A | 11/2006 |
| JP | 2011-115724 A | 6/2011 |
| JP | 2012-520167 A | 9/2012 |
| JP | 2014-526380 A | 10/2014 |
| JP | 2015-16391 A | 1/2015 |
| JP | 6151993 B2 | 6/2017 |
| WO | 2014/191160 A1 | 12/2014 |

OTHER PUBLICATIONS

International Search Report dated Mar. 10, 2015, issued in counterpart International Application No. PCT/JP2015/050280 (2 pages).

* cited by examiner

[FIG. 1]
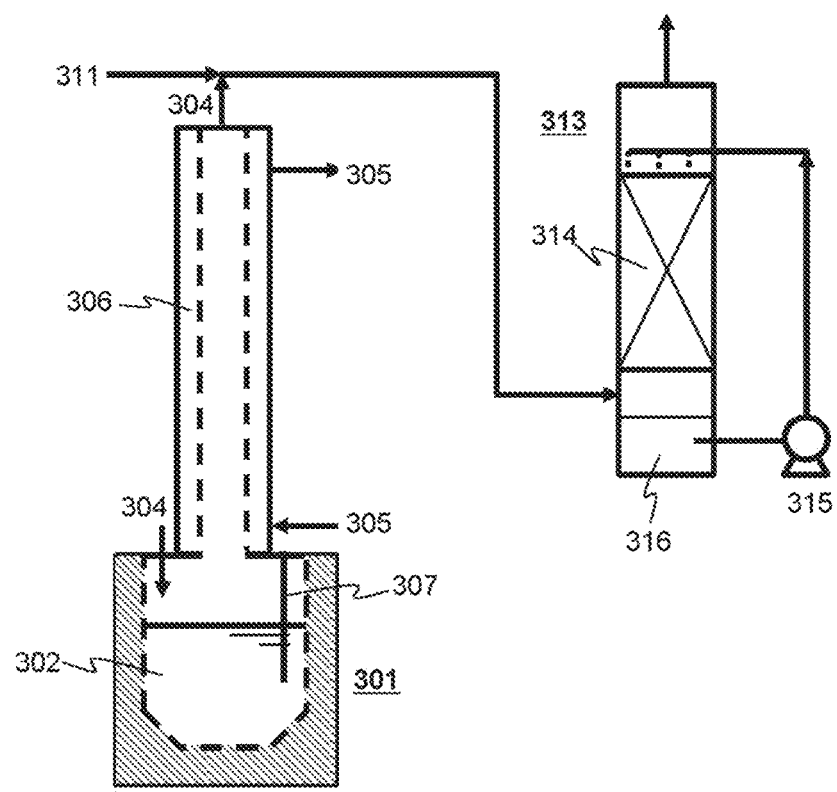

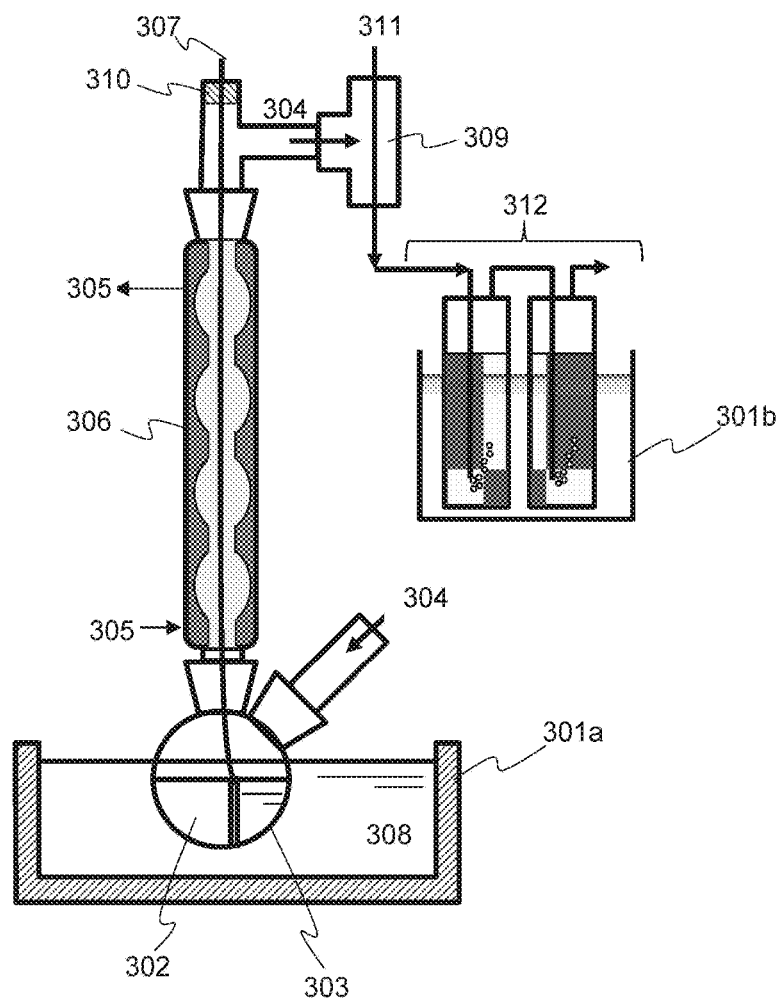
[FIG. 2]

[FIG. 3]
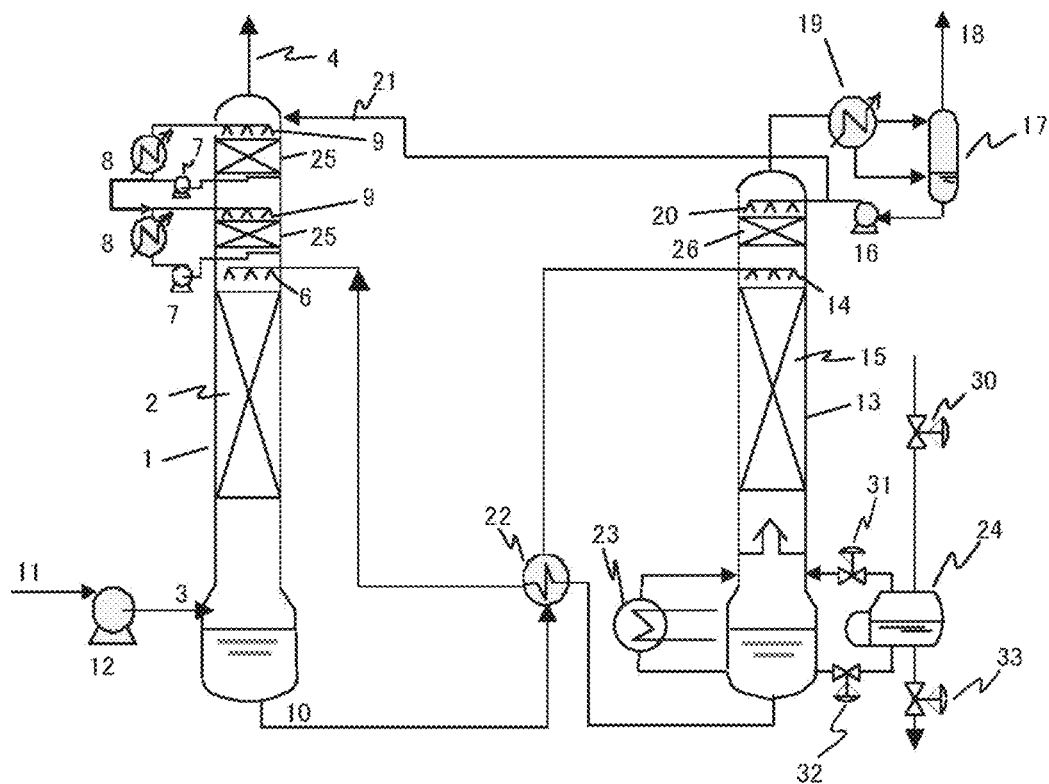

METHOD AND DEVICE FOR TREATING NITROSO COMPOUND

TECHNICAL FILED

The present invention relates to a processing method for decomposing a nitroso compound, a processing apparatus for decomposing a nitroso compound, and a method for recovering carbon dioxide in a gas to be treated. More specifically, the present invention relates to a method for decomposing, at low temperature and with high efficiency, a nitroso compound into amines, the nitroso compound being derived from amines that is contained in a $CO_2$ absorption liquid used for recovering carbon dioxide in a gas exhausted from a combustion equipment such as a boiler, or that is contained in a reclaimer remaining liquid that remains upon converting a heat stable salt in the $CO_2$ absorption liquid into amines by reclaiming process.

BACKGROUND ART

In a thermal power plant or the like, a fossil fuel is combusted, and therefore a large volume of carbon dioxide ($CO_2$) is generated. With regard to carbon dioxide, as a substance causing warming, control of emissions thereof has advanced in individual countries. As a method for recovering carbon dioxide, a method for absorption thereof using a liquid containing amines such as alkanolamine is currently known as the method closest to practical application (for example, see Patent Literature 1).

A combustion exhaust gas contains, in addition to $CO_2$, and acid gas component such as HCl (hydrogen chloride), $NO_x$ (nitrogen oxides), $SO_x$ (sulfur oxides) and the like; oxygen, nitrogen, water vapor or the like. If the combustion exhaust gas is brought into contact with $CO_2$ absorption liquid containing amines, not only $CO_2$ but also the acid gas component is absorbed into the $CO_2$ absorption liquid. If the acid gas component is bonded with amines, an inorganic acid salt is formed. For example, hydrochlordie salt is formed from HCl, nitrate is formed from $NO_x$, or sulfate is formed, from $SO_2$. Moreover, if an organic acid, such as formic acid, oxalic acid, acetic acid and the like, which is produced, as a by-product by decomposition of amines, is bonded with amines, an Organic, acid salt is formed. Such an organic facial salt and an inorganic acid salt are a thermally stable salt (hereinafter, referred, to as a heat stable salt in several cases). The heat stable salt causes corrosion of metal or reduction of $CO_2$ absorption capacity. Therefore, the heat stable salt is removed by reclaiming process or the like.

While the $CO_2$ absorption liquid containing amines is used for recovery of carbon dioxide from the combustion exhaust gas, part of amines can be nitrosated in several cases. Moreover, a reclaimer remaining liquid that remains upon converting the heat stable salt in the $CO_2$ absorption liquid in amines by reclaiming process contains the heat stable salt, amines not wholly used for recovery and a nitroso compound produced by nitrosation of amines.

Incidentally, the nitroso compound derived from amines absorbs carbon dioxide in a lower volume than amines of an origin absorb, and reduces carbon dioxide recovery efficiency. Therefore, researches on removing such a nitroso compound have been conducted in various manners. For example, Patent Literature 2 discloses a method for decomposing nitrosamine by irradiating a composition containing the nitrosamine with electromagnetic energy. Moreover, Patent Literature 3 discloses a method comprising heating and decomposing nitrosamine. Most of nitrosamines have a higher boiling point than original amines have. For example, a boiling point of N-nitrosodimethylamine produced by nitrosation of dimethylamine (boiling point: 7.0° C.) is 151 to 154° C., and a boiling point of N-nitrosodiethylamine produced by nitrosation of diethylamine (boiling point: 55.5° C.) is 177° C. A nitrosated compound of amines is required to be heated at high temperature for thermal decomposition. In a method for thermally decomposing the nitrosated compound of amines, amines being a main component in the $CO_2$ absorption liquid are also thermally decomposed together, and therefore loss of amines is large. In a carbon dioxide recovery apparatus in which an ion-exchange resin method or an electrodialysis method is employed, facilities for heating a material at high temperature are not installed, and therefore the facilities for heating the material at high temperature are required for practicing a conventional method for thermally decomposing the nitroso compound. In a carbon dioxide recovery apparatus in which a distillation method is employed for regenerating amines, the nitroso compound contained in the reclaimer remaining liquid discharged from a reclaiming apparatus is required to be treated at low cost.

CITATION LIST

Patent Literatures

Patent Literature 1: JP 3529855 B
Patent Literature 2: WO 2013/043802 A
Patent Literature 3: WO 2012/104137 A

SUMMARY OF THE INVENTION

Problems to be Solved by the Invention

An object of the present invention is to provide a method capable of obtaining amines by decomposing, at low temperature and with high efficiency, a nitroso compound derived from amines that is contained in a $CO_2$ absorption liquid used for recovering carbon dioxide in a gas exhausted from a combustion equipment such as a boiler, or that is contained in a reclaimer remaining liquid that remains upon converting a heat stable salt in the $CO_2$ absorption liquid into amines by reclaiming process.

Another object of the present invention is to provide a method for recovering carbon dioxide in which consumption of amines having $CO_2$ absorption capacity is small.

Means for Solving the Problems

The present inventors have continued to conduct research to achieve the above-described objects, and as a result, the present inventors have completed the present invention including embodiments below.

[1] A method for decomposing a nitroso compound, comprising:
adding an aqueous solution containing hydrogen halide to a liquid to be treated that contains the nitroso compound in such a manner that the hydrogen halide is present in an amount of 2 mol or more and 20 mol or less per mol of a nitroso group in the nitroso compound; and
subsequently heating the resulting liquid to be treated at a temperature of not lower than 75° C. and not higher than a boiling point of water under ordinary pressure.

[2] The method for decomposing the nitroso compound according to [1], wherein the hydrogen halide is at least one selected from the group consisting of hydrogen chloride, hydrogen bromide and hydrogen iodide.

[3] The method for decomposing the nitroso compound according to [1] or [2], wherein the liquid to be treated is a remaining liquid obtained upon reclaiming an aqueous solution of amines used for absorbing carbon dioxide in a combustion exhaust gas.

[4] The method for decomposing the nitroso compound according to any one of [1] to [3], further comprising, when the liquid to be treated is basic, neutralizing the liquid to be treated using at least one selected from the group consisting of hydrochloric acid, hydrobromic acid, hydroiodic acid, sulfuric acid and nitric acid before the heating of the liquid.

[5] A method for recovering carbon dioxide in a gas to be treated, comprising:
a step (I) of bringing the gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid;
a step (II) of heating the $CO_2$ rich absorption liquid for releasing the carbon dioxide to regenerate the $CO_2$ lean absorption liquid;
a step (IIIa) of adding an aqueous solution containing hydrogen halide to part of the $CO_2$ lean absorption liquid regenerated in the step (II) in such a manner that the hydrogen halide is present in an amount of 2 mol or more and 20 mol or less per mol of a nitroso group in a nitroso compound contained in the $CO_2$ lean absorption liquid, and subsequently heating the $CO_2$ lean absorption liquid at a temperature of not lower than 75° C. and not higher than a boiling point on water under ordinary pressure; and
a step (IV) of providing, to the step (I), another of the $CO_2$ lean absorption liquid regenerated in the step (II) and/or the $CO_2$ lean absorption liquid heated in the step (IIIa).

[6] A method for recovering carbon dioxide in a gas to be treated, comprising:
a step (I) of bringing the gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid;
a step (II) of heating the $CO_2$ rich absorption liquid for releasing the carbon dioxide to regenerate the $CO_2$ lean absorption liquid;
a step (V) of reclaiming part of the $CO_2$ lean absorption liquid regenerated in the step (II) to remove a heat stable salt;
a step (IIIb) of adding an aqueous solution containing hydrogen halide to a remaining liquid obtained in the step (V) in such a manner that the hydrogen halide is present in an amount of 2 mol or more and 20 mol or less per mol of a nitroso group in a nitroso compound contained in the remaining liquid, and subsequently heating the remaining liquid at a temperature of not lower than 75° C. and not higher than a boiling point of water under ordinary pressure to recover amines; and
a step (IV) of providing, to the step (I), another of the $CO_2$ lean absorption liquid regenerated in the step (II) and/or the amines recovered in the step (IIIb).

[7] A processing apparatus for decomposing a nitroso compound, comprising:
a reaction vessel for heating a liquid to be treated that contains the nitroso compound at a temperature of not lower than 75° C. and not higher than a boiling point of water under ordinary pressure in the presence of hydrogen halide in an amount of 2 mol or more and 20 mol or less per mol of a nitroso group in the nitroso compound so as to decompose the nitroso compound; a gas passage for discharging a decomposition gas produced in the decomposition from the reaction vessel by introducing a carrier gas into a gas-phase portion of the reaction vessel; a condenser for cooling the decomposition gas to condense water vapor; and a halogen recovery apparatus for recovering a halogen gas in the decomposition gas.

[8] The processing apparatus for decomposing the nitroso compound according to [7], wherein the halogen recovery apparatus works to absorb the halogen gas into an aqueous solution containing at least one selected from the group consisting of alkali metal hydroxide, magnesium hydroxide and alkaline earth metal hydroxide.

Advantageous Effects of the Invention

According to the method of the present invention, a nitroso compound can be decomposed at low temperature and with high efficiency into amines, the nitroso compound being derived from amines that is contained in a $CO_2$ absorption liquid used for recovering carbon dioxide in a gas exhausted from a combustion equipment such as a boiler, or that is contained in a reclaimer remaining liquid that remains upon converting a heat stable salt in the $CO_2$ absorption liquid into amines by reclaiming process.

According to the method of the present invention, the amount of amines to be lost in recovery of carbon dioxide can be reduced.

BRIEF DESCRIPTION OF THE DRAWINGS

FIG. 1 is a diagram showing one embodiment of an apparatus for practicing a method for decomposing a nitroso compound.

FIG. 2 is a diagram showing another embodiment of an apparatus for practicing a method for decomposing a nitroso compound.

FIG. 3 is a diagram showing one embodiment of an apparatus for practicing a method for recovering carbon dioxide according to the present invention.

EMBODIMENTS FOR CARRYING OUT THE INVENTION

A method for decomposing a nitroso compound according to one embodiment of the present invention comprises adding an aqueous solution containing hydrogen halide to a liquid to be treated that contains the nitroso compound in such a manner that the hydrogen halide is present in an amount of 2 mol or more and 20 mol or less per mol of a nitroso group in the nitroso compound, and subsequently heating the resulting liquid to be treated at a temperature of not lower than 75° C. and not higher than a boiling point of water under ordinary pressure.

The nitroso compound is obtained by reduction of a nitro compound or nitrosation of amines. Among them, the nitroso compound obtained by nitrosation of amines is preferred in the present invention.

As amines, mentioned are a primary amine, a secondary amine and a tertiary amine.

Specific examples of the primary amine can include monoalkanolamine such as monomethanolamine, monoethanolamine and the like; and alkylamine such as methylamine, ethylamine and the like.

Specific examples of the secondary amine can include dialkylamine such as dimethylamine, diethylamine, methylethylamine, t-butylethylamine, dibutylamine and the like; dialkanolamine such as dimethanolamine, diethanolamine and the like; N-alkyl-N-(hydroxylalkyl)amine such as N-methyl-N-(hydroxyethyl)amine, N-ethyl-N-(hydroxyethyl)amine, N-ethyl-N-(hydroxybutyl)amine, N-isopropyl-N-(hydroxyethyl)amine, N-methyl-N-(hydroxypropyl) amine and the like; and cyclic amine such as heptamethyleneimine, piperazine, piperizine, morpholine and the like.

Specific examples of the tertiary amine can include trialkylamine such as trimethylamine, triethylamine and the like, trialkanolamine such as trimethanolamine, triethanolamine and the like; and cyclic amine such as quinuclidine, pyridine and the like.

Among them, alkanlolamines are preferred, and N-hydroxylalkylamine or N-alkyl-N-hydroxylalkylamine is further preferred.

As the nitroso compound contained in the liquid to be treated used in the present invention, mentioned can be nitroso compounds (nitrosoalkanes) represented by R—N=O and produced by oxidation of a primary amine ($RNH_2$), and N-nitroso compounds (N-nitrosamines) represented by RNH—N=O or $R_2N$—N=O and produced by a reaction of a primary amine ($RNH_2$) or a secondary amine ($R_2NH$) with nitrous acid, wherein R is an N-substituent such as an alkyl group, a hydroxyalkyl group and the like. The nitroso compound represented by R—N=O, when R is a primary alkyl group or a secondary alkyl group, may be varied into an oxime. Therefore, in the present invention, the tautomer is also included in the nitroso compound. Moreover, nitrosoalkanes may be formed into a dimer. Therefore, in the present invention, the dimer is also included in the nitroso compound. N-nitrosamines represented by RNH—N=O is an unstable substance and may be converted into diazohydroxide by decomposition at room temperature. Therefore, in the present invention, the tautomer is also included in the nitroso compound.

Specific examples of the nitroso compound can include N-nitrosodiethanolamine, N-nitrosoheptamethyleneimine, N-nitrosodimethylamine, N-nitrosodiethylamine, N-nitrosomethylhydroxyethylamine, N-ethyl-N-(2-hydroxyethyl)nitrosamine, N-tert-butyl-N-ethylnitrosamine, N-nitrosodibutylamine, N-ethyl-N-(4-hydroxybutyl)nitrosamine, N-butyl-N-(4-hydroxybutyl)nitrosamine, N-nitrosomorpholine and the like. Among these, the nitroso compound soluble in or miscible with water is preferably used as a decomposition object in the method according to the present invention.

As the liquid to be treated that contains the nitroso compound, an aqueous solution of amines used for absorbing carbon dioxide in a combustion exhaust gas (hereinafter, referred to as a $CO_2$ absorption liquid in several cases), or a remaining liquid obtained upon performing operation (reclaiming) for removing a heat stable salt from the $CO_2$ absorption liquid (hereinafter, referred to as a reclaimer remaining liquid in several cases) is preferably used. The $CO_2$ absorption liquid is an aqueous solution at least containing amines as a main component and the nitroso compound as an impurity. The reclaimer remaining liquid is an aqueous solution containing the heat stable salt, amines not wholly used for recovery and the nitroso compound produced by nitrosation of amines.

A boiling point of the nitroso compound is higher than a boiling point of amines in many cases. Therefore, the decomposition method of the present invention is preferably applied after concentrating the nitroso compound by distilling amines away from the liquid to be treated. If the amount of amines in the liquid to be treated is small, the amount of hydrogen halide consumed by a reaction with the amines is reduced, and the amount of hydrohalic acid to be added thereto can be reduced. Moreover, amines that are unnecessarily decomposed by heating for decomposing the nitroso compound can be reduced. Moreover, the amount of water in the liquid to be treated is also preferably reduced. The reason is that, as described later, nitrosyl halide produced as a by-product may react with water to form nitrous acid, and the nitrous acid may cause nitrosation of amines again.

As the aqueous solution containing hydrogen halide (hydrohalic acid) used in the present invention, mentioned can be at least one selected from the group consisting of a hydrogen chloride aqueous solution (hydrochloric acid), a hydrogen bromide aqueous solution (hydrobromic acid) and a hydrogen iodide aqueous solution (hydroiodic acid).

The amount of hydrohalic acid to be added to the liquid to be treated is an amount, in which hydrogen halide is theoretically present in the liquid, of 2 mol or more and 20 mol or less, and preferably 3 mol or more and 20 mol or less, per mol of a nitroso group. In addition, the amount of the nitroso group includes the amount of the tautomer. Moreover, when the liquid to be treated contains a base such as amines, part of hydrogen halide added thereto is consumed by a reaction with the base. The amount of hydrohalic acid to be added to the liquid to be treated is determined in taking into account the amount of this consumption.

The amount of presence of hydrogen halide is adjusted in the above-described range. Thus, amines regenerated from the nitroso compound react with the hydrogen halide to form heat stable salts, and unnecessary thermal decomposition of amines regenerated from the nitroso compound can be prevented.

Moreover, pH of the liquid to be treated is preferably less than 5, further preferably less than 3, and still further preferably less than 2. In the case of using the liquid to be treated that is basicity, such as the remaining liquid obtained upon performing reclaiming process with adding the base, the liquid to be treated is preferably neutralized before heating the liquid. For neutralization, at least one selected from the group consisting of hydrochloric acid, hydrobromic acid, hydroiodic acid, sulfuric acid and nitric acid is preferably used. Heat is generated by a neutralization reaction, and therefore energy for heating the liquid can be saved.

The decomposition of the nitroso compound is conducted by heating the liquid at a temperature of not lower than 75° C. and not higher than the boiling point of water under ordinary pressure. Details of a decomposition mechanism of the nitroso compound according to the present invention is not known for certain, but is presumed to be decomposed according to a chemical reaction as shown in the following formula, for example. The nitroso compound can be converted into original amines by the decomposition.

[Formula 1]

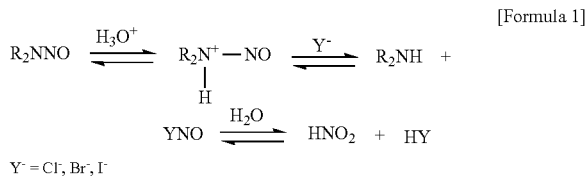

YNO (nitrosyl halide) produced as a by-product in the decomposition reaction may be reacted with water to produce nitrous acid as a by-product. Moreover, with regard to nitrosyl halide, a boiling point thereof is, for example, −6.4° C. in nitrosyl chloride, which is lower than the boiling point of amines in many cases, and therefore nitrosyl halide can be vaporized and removed by adjusting a heating temperature for decomposing the nitroso compound.

Among amines contained in the liquid to be treated, amines formed into the heat stable salt by reacting with hydrogen halide are not decomposed by heating for decomposing the nitroso compound. However, amines not formed into the heat stable salt are somewhat decomposed by heating for decomposing the nitroso compound, and therefore the heating temperature is preferably as low as possible, but if the temperature is excessively low, a rate of the decomposition reaction is decreased. Therefore, the heating temperature is 75° C. or higher, preferably 80° C. or higher, and further preferably 85° C. or higher, and not higher than the boiling point of water (about 100° C.), and preferably lower than the boiling point of water.

A method for recovering carbon dioxide in a gas to be treated according to a first embodiment of the present invention, comprises a step (I) of bringing the gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid, a step (II) of heating the $CO_2$ rich absorption liquid for releasing the carbon dioxide to regenerate the $CO_2$ lean absorption liquid, a step (IIIa) of adding an aqueous solution containing hydrogen halide to part of the $CO_2$ lean absorption liquid regenerated in the step (II) in such a manner that the hydrogen halide is present in an amount of 2 mol or more and 20 mol or less per mol of a nitroso group in a nitroso compound contained in the $CO_2$ lean absorption liquid, and subsequently heating the $CO_2$ lean absorption liquid at a temperature of not lower than 75° C. and not higher than a boiling point of water under ordinary pressure, and a step (IV) of providing, to the step (I), another of the $CO_2$ lean absorption liquid regenerated in the step (II) and/or the $CO_2$ lean absorption liquid heated in the step (IIIa).

A method for recovering carbon dioxide in a gas to be treated according to a second embodiment of the present invention, comprises a step (I) of bringing the gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid, a step (II) of heating the $CO_2$ rich absorption liquid for releasing the carbon dioxide to regenerate the $CO_2$ lean absorption liquid, a step (V) of reclaiming part of the $CO_2$ lean absorption liquid regenerated in the step (II) to remove a heat stable salt, a step (IIIb) of adding an aqueous solution containing hydrogen halide to a remaining liquid obtained in the step (V) in such a manner that the hydrogen halide is present in an amount of 2 mol or more and 20 mol or less per mol of a nitroso group in a nitroso compound contained in the remaining liquid, and subsequently heating the remaining liquid at a temperature of not lower than 750° C. and not higher than a boiling point of water under ordinary pressure to recover amines, and a step (IV) of providing, to the step (I), another of the $CO_2$ lean absorption liquid regenerated in the step (II) and/or the amines recovered in the step (IIIb).

The method for recovering carbon dioxide in the gas to be treated according to the embodiment of the present invention can be applied in the apparatus as shown in FIG. 3, for example.

In the present invention, the step (I), the step (II) and step (IV) are ordinarily performed continuously and simultaneously.

Step (I):

A gas 11 to be treated is fed to a bottom portion 3 of a $CO_2$ absorption column 1 by a blower 12, ascends in a packed bed 2, and is vented as a treated gas 4 from a top portion. A pressure of the gas 11 to be treated may be more than ordinary pressure, or ordinary pressure. A temperature of the gas 11 to be treated is preferably 100° C. or lower. The $CO_2$ lean absorption liquid containing amines is showered above the packed bed 2 from a nozzle 6, brought into contact with the gas to be treated in the packed bed 2, absorbs carbon dioxide in the gas to be treated, and is accumulated in a bottom portion 10. The liquid accumulated in the bottom portion 10 is rich in carbon dioxide, and is referred to as the $CO_2$ rich absorption liquid.

Step (II):

The $CO_2$ rich absorption liquid discharged from the bottom portion 10 is heated in a heat exchanger 22 and showered above a packed bed 15 in a regeneration column ($CO_2$ desorption column) 13 from a nozzle 14. The showered liquid descends in the packed bed 15 and is accumulated in a bottom portion of the $CO_2$ desorption column. The liquid accumulated in the bottom portion of the $CO_2$ desorption column has a small content of carbon dioxide, and is referred to as the $CO_2$ lean absorption liquid. At a column bottom, a reboiler 23 is installed. A vapor vaporized in the reboiler ascends in the packed bed 15 to heat the $CO_2$ rich absorption liquid descending in the packed bed 15 to release carbon dioxide. A mist contained in the released carbon dioxide is removed in a water washing unit 26, and the carbon dioxide is discharged from a top portion of the $CO_2$ desorption column. Further, water is collected in a separator 17, the carbon dioxide is delivered to a next process through a pipe 18, and the collected water is supplied to the water washing unit 26 in the $CO_2$ desorption column or the nozzle 9 in the top portion of the $CO_2$ absorption column.

Step (IV):

The $CO_2$ lean absorption liquid accumulated in the bottom portion of the $CO_2$ desorption column is cooled in the heat exchanger 22, and returned to the $CO_2$ absorption column 1.

In the first embodiment of the present invention, the step (IIIa) may be performed continuously all the time, but from a viewpoint of energy saving, is preferable performed when $CO_2$ absorption capacity of the $CO_2$ absorption liquid is reduced.

Moreover, in the second embodiment of the present invention, the step (V) and the step (IIIb) may be performed continuously all the time, but from a viewpoint of energy saving, is preferably performed when the $CO_2$ absorption capacity of the $CO_2$ absorption liquid is reduced.

As described above, reduction of the $CO_2$ absorption capacity of the $CO_2$ absorption liquid is caused by an increase of the amount of the heat stable salt and/or the nitroso compound in the $CO_2$ absorption liquid. The amount of the heat stable salt and the nitroso compound can be measured by a publicly known method.

When the amount of the heat stable salt in the $CO_2$ absorption liquid is relatively small and the amount of the nitroso compound in the $CO_2$ absorption liquid is relatively large, the step (IIIa) can be performed.

Step (IIIa):

For example, part of the $CO_2$ lean absorption liquid is discharged from the bottom portion of the $CO_2$ desorption column in the apparatus as shown in FIG. 3. The discharged $CO_2$ lean absorption liquid is transferred to a nitroso compound decomposition device as described later, and the nitroso compound can be decomposed in the device.

As another method, when a valve 30 is opened in the apparatus as shown in FIG. 3, water vapor is delivered to a heat-transfer tube of a reclaiming device 24. The $CO_2$ lean absorption liquid discharged from the bottom portion of the $CO_2$ desorption column 13 is heated in the heat-transfer tube of the reclaiming device 24. Then, amines and water contained in the $CO_2$ lean absorption liquid are vaporized and returned to the $CO_2$ desorption column. The heat stable salt and the nitroso compound are concentrated. Hydrohalic acid is supplied to the concentrated liquid, and the concentrated liquid is heated in the presence of hydrogen halide in an amount of 2 mol or more and 20 mol or less per mol of a nitroso group in the nitroso compound contained in the $CO_2$ lean absorption liquid. Thus, the nitroso compound is converted into original amines. In addition, the heating is performed at a temperature of not lower than 75° C. and not higher than the boiling point of water under ordinary pressure. Here, the reclaiming device 24 is desirably isolated from the $CO_2$ desorption column 13, for example, by closing valves 31, 32 in pipings between the device 24 and the desorption column 13 after concentrating the liquid to be treated, and during supplying hydrohalic acid and heating at ordinary pressure. Transfer of the vapor and the liquid from the device 24 to the $CO_2$ desorption column 13 is prevented. On this occasion, the gas in the reclaiming device 24 may be discharged after waste gas treatment is applied thereto, or may be released into atmosphere together with the treated gas 4. After completion of the above-described treatment, the valves 31, 32 are opened, and the step can be returned to ordinary reclaiming operation, and amine halide contained in the liquid to be treated can be converted to regenerate amine.

Step (VI):

When the heat stable salt remains in the concentrated liquid heated in the step (IIIa), the salt is discharged, as sludge, from the reclaiming device 24 by opening a valve 33, or the reclaiming (step (V)) is performed.

When the amount of the heat stable salt in the $CO_2$ absorption liquid is relatively large, the step (V) can be performed.

Reclaiming (step (V)) is performed as described below, for example. An alkali component (for example, alkali metal hydroxide, alkali metal carbonate or the like) is added to the $CO_2$ lean absorption liquid containing the heat stable salt in the reclaiming device 24, and the resultant mixture is heated to convert the heat stable salt for generating amines. The regenerated amines can be vaporized and returned to the $CO_2$ desorption column.

Step (IIIb):

The remaining liquid obtained in the step (V) is discharged from the reclaiming device 24. The discharged remaining liquid is transferred to a processing apparatus for decomposing the nitroso compound as described below, and the nitroso compound can be decomposed.

A processing apparatus for decomposing a nitroso compound according to one embodiment of the present indention, comprises a reaction vessel for heating a liquid to be treated that contains the nitroso compound (the above-described remaining liquid or the like) at a temperature of not lower than 75° C. and not higher than a healing point of water under ordinary pressure in the presence of hydrogen halide in an amount of 2 mol or more and 20 mol or less per ml of a nitroso group in the nitroso compound to decompose the nitroso compound, a gas passage for discharging a decomposition gas produced in the decomposition from the reaction vessel by introducing a carrier gas into a gas-phase portion of the reaction vessel, a condenser for cooling the decomposition gas to condense water vapor, and a halogen recovery apparatus for recovering a halogen gas in the decomposition gas. The carrier gas is not particularly limited as long as the gas does not react with the halogen gas, Specific examples thereof can include a nitrogen gas, air and the like. Hydrogen halide can be supplied thereto by adding hydrohalic acid to the liquid to be treated that is put in the reaction vessel. In the condenser, condensed water can be returned to the reaction vessel.

For the halogen recovery apparatus, a publicly known gas absorption apparatus can be adopted. As the liquid (hereinafter, referred to as a halogen absorption liquid in several cases), to be used for gas absorption, an aqueous solution containing at least one selected from the group consisting of alkali metal hydroxide, magnesium hydroxide and alkaline earth hydroxide is preferred. When the decomposition gas contains NO or the like, the decomposition gas is preferably subjected to denitration for being released into atmosphere.

Hereinafter, the present invention is more specifically described by illustrating Examples. The present invention is not limited by the Examples described below.

The apparatus used in Examples is described only as an example, and does not limit the scope of the present invention. For example, with regard to a constant temperature water tank for heating, a flask as a reaction vessel, an impinger as a halogen recovery apparatus and the like, even if other instruments each having an identical function are used, similar results can be obtained.

The amount of a nitroso compound was measured using a GC (Gas Chromatograph)-TEA (Thermal Energy Analysis) instrument (TEA-800, made by Ellutia Limited).

The amount of an amine compound was measured using an ion chromatograph (ICS-1500, made by DIONEX Corporation). In addition, the amount of the amine compound includes an amount converted into mass of the amine compound for amine chloride.

Example 1

An experiment was conducted using a device as shown in FIG. 2.

A liquid to be treated that contains 76.5% by mass of diethanolamine ($C_4H_{11}NO_2$, hereinafter, DEA, molecular weight: 105 g/mol, boiling point: 268.8° C., (according to MSDS of Showa Chemical Co., Ltd.)), 13.5% by mass of water and 10% by mass of nitrosodiethanolamine ($C_4H_{10}N_2O_3$, hereinafter, NDEA, molecular weight: 134 g/mol) was prepared.

As hydrohalic acid, hydrochloric acid (HCl concentration: 36% by mass) was arranged.

In a flask 303, 10 g of the liquid to be treated and 9.65 g of hydrochloric acid (total of mass to be 1 mol per mol of DEA and mass to be 3 mol per mol of NDEA) were charged. The flask was placed in a constant temperature water tank 301a. A condenser 306 was installed to the flask, and water 305 at 20° C. was circulated. Moreover, as a carrier gas 304, air (dew point: 20° C.) was supplied to a gas-phase portion of the flask 303 at 0.2 NL/min. Further, as a dilution gas 311, air was supplied in a T-tube 309 at 2 NL/min.

In an impinger 312, a 0.1N NaOH aqueous solution was put. A gas discharged through the T-tube was passed through the impinger 312.

A temperature of the constant temperature water tank 301a was set at 95° C. and the liquid to be treated was heated for 24 hours to perform a decomposition reaction. Mass and composition of a liquid remaining in the flask were measured. Then, 1.0 g of NDEA changed to 1.6 mg and 7.65 g of DEA changed to 8.43 g. Thus, 99.8% of NDEA was decomposed.

Example 2

A decomposition reaction was performed in the same manner as in Example 1 except that the amount of hydrochloric acid (HCl concentration 36% by mass) was changed to 8.89 g (total of mass to be 1 mol per mol of DEA and mass to be 2 mol per mol of NDEA). Mass and composition of a liquid remaining in a flask were measured. Then, 1.0 g of NDEA changed to 54 mg, and 7.65 g of DEA changed to 8.39 g. Thus, 94.6% of NDEA was decomposed.

Example 3

A decomposition reaction was performed in the same manner as in Example 1 except that the amount of hydrochloric acid (HCl concentration: 36% by mass) was changed to 22.50 g (total of mass to be 1 mol per mol of DEA and mass to be 20 mol per mol of NDEA). Mass and composition of a liquid remaining in a flask were measured. Then, 1.0 g of NDEA changed to 1.3 mg and 7.65 g of DEA changed to 8.43 g. Thus, 99.9% of NDEA was decomposed.

Example 4

A decomposition reaction was performed in the same manner as in Example 1 except that 9.65 g of hydrochloric acid was changed to 14.80 g of hydrobromic acid (HBr concentration: 48% by mass) (total of mass to be 1 mol per mol of DEA and mass to be 2 mol per mol of NDEA). Mass and composition of a liquid remaining in a flask were measured. Then, 1.0 g of NDEA changed to 1.6 mg and 7.65 g of DEA changed to 8.43 g. Thus, 99.9% of NDEA was decomposed.

Comparative Example 1

A decomposition reaction was attempted in the same manner as in Example 1 except that the amount of hydrochloric acid was changed to 0 g. Mass and composition of a liquid remaining in a flask were measured. No change was found in mass of NDEA and DEA. No NDEA was decomposed at all.

Comparative Example 2

A decomposition reaction was performed in the same manner as in Example 1 except that the amount of hydrochloric acid (HCl concentration: 36% by mass) was changed to 7.38 g (mass to be 1 mol per mol of DEA). Mass and composition of a liquid remaining in a flask were measured. No change was found in mass of NDEA and DEA. No NDEA was decomposed at all. All of hydrochloric acid added thereto were consumed in a neutralization reaction.

Comparative Example 3

A decomposition reaction was performed in the same manner as in Example 1 except that the amount of hydrochloric acid was changed to 8.13 g (total of mass to be 1 mol per mol of DEA and mass to be 1 mol per mol of NDEA). Mass and composition of a liquid remaining in a flask were measured. Then, 1.0 g of NDEA changed to 0.5 g and 7.65 g of DEA changed to 8.04 g. Thus, 50% of NDEA was decomposed.

Comparative Example 4

A decomposition reaction was performed in the same manner as in Example 1 except that a preset temperature of a constant temperature water tank 301a was changed to 70° C. Mass and composition of a liquid remaining in a flask were measured. No change was found in mass of NDEA and DEA. No NDEA was decomposed at all.

Comparative Example 5

A decomposition reaction was performed in the same manner as in Example 1 except that 9.65 g of hydrochloric acid was changed to 4.77 g of sulfuric acid ($H_2SO_4$ concentration: 98% by mass) (total of mass to be 0.5 mol per mol of DEA and mass to be 1.5 mol per mol of NDEA). Mass and composition of a liquid remaining in a flask were measured. No change was found in mass of NDEA and DEA. No NDEA was decomposed at all.

Example 5

A decomposition reaction was performed in the same manner as in Example 1 except that a preset temperature of a constant temperature water tank 301a was changed to 80° C. Mass and composition of a liquid remaining in a flask were measured. Then, 1.0 g of NDEA changed to 0.3 g and 7.65 g of DEA changed to 8.20 g. Thus, 70% of NDEA was decomposed.

Example 6

A decomposition reaction was performed in the same manner as in Example 1 except that 9.65 g of hydrochloric acid was changed to 3.65 g of sulfuric acid ($H_2SO_4$ concentration: 98% by mass) (mass to be 0.5 mol per mol of DEA) and 2.27 g of hydrochloric acid (mass to be 3 mol per mol of NDEA), and the sulfuric acid was first added to a liquid to be treated, and then the hydrochloric acid was added thereto. Mass and composition of a liquid remaining in a flask were measured. Then, 1.0 g of NDEA changed to 1.6 mg, and 7.65 g of DEA changed to 8.43 g. Thus, 99.8% of NDEA was decomposed. The liquid to be treated was neutralized by adding the sulfuric acid thereto.

Example 7

An experiment was conducted using an apparatus as shown in FIG. 1.

A liquid to be treated that was composed of 765 g of DEA, 135 g of water and 100 g of NDEA was prepared.

As hydrohalic acid, hydrochloric acid (HCl concentration: 36% by mass) was arranged.

In a reaction vessel 301 having an internal volume of 10 L, 1,000 g of the liquid to be treated and 965 g (total of mass to be 1 mol per mol of DEA and mass to be 3 mol per mol of NDEA) of hydrochloric acid, were charged. As a carrier gas 304, air (dew point: 20° C.) was supplied to a gas-phase portion of the reaction vessel 301 at 20 NL/min. Further, as a dilution gas 311, air was supplied at 200 NL/min.

A gas was introduced into a bottom portion of a halogen absorption column 313, and a 0.1 N NaOH aqueous solution Was showered above a top portion of a packed bed 314.

A temperature of the reaction vessel was set at 95° C., and the liquid to be treated was heated for 24 hours to allow decomposition reaction. Mass and composition of a liquid remaining in the reaction vessel were measured. Then, 100 g of NDEA changed to 160 mg, and 765 g of DEA changed to 825 g. Thus, 99.8% of NDEA was decomposed. Even when scale-up was made, the experimental results of Example 1 were reproduced. A gas discharged from a top portion of the halogen absorption column 313 contained practically no halogen gas.

As the results show, when the liquid is heated at a temperature of not lower than 75° C. and not higher than a boiling point of water under ordinary pressure in such a manner that hydrogen halide is present in an amount of 2 mol or more and 20 mol or less per mol of a nitroso group in a nitroso compound, the nitroso compound can be decomposed with high efficiency to be converted into amines.

In the liquid to be treated that contains amines, hydrogen halide is required to be added in taking account the amount of hydrogen halide consumed in neutralization of amines (Comparative Examples 2 and 3). Moreover, even when amines are neutralized with sulfuric acid or the like, if the hydrogen halide is adjusted to be present in an amount of 2 mol or more and 20 mol or less per mol of a nitroso group in the nitroso compound, the nitroso compound can be decomposed with high efficiency to be converted into amines.

In the method of the present invention, a heating temperature is as low as a temperature of not lower than 75° C. and not higher than a boiling point of water. Therefore, if the method of the present invention is employed in a carbon dioxide recovery apparatus in which amine regeneration by an electrodialysis method or an ion-exchange membrane method is adopted, amines can be recovered from the nitroso compound with high efficiency even without installing an additional apparatus.

EXPLANATION OF SYMBOLS 301a, 301b: Constant Temperature Water Tank;
302: Liquid to be Treated;
303: Flask;
304: Carrier Gas;
305: Cooling Water;
306: Condenser;
307: Thermocouple;
308: Water;
309: T-Tube;
310: Airtight Stopper;
311: Dilution Gas;
312: Impinger;
301: Reaction Vessel;
313: Halogen Absorption Column;
314: Packed bed;
315: Pump;
316: Halogen Absorption Liquid

The invention claimed is:

1. A method for decomposing a nitroso compound, the method comprising:
adding an aqueous solution containing hydrogen halide to a liquid to be treated that contains the nitroso compound so as to obtain a mixture, wherein an amount of the hydrogen halide in the mixture is 2 mol or more and 20 mol or less per mol of a nitroso group in the nitroso compound; and
subsequently heating the mixture at a temperature of not lower than 75° C. and not higher than 100° C. and under ordinary pressure to decompose the nitroso compound.

2. The method for decomposing the nitroso compound according to claim 1, wherein the hydrogen halide is at least one selected from the group consisting of hydrogen chloride, hydrogen bromide and hydrogen iodide.

3. The method for decomposing the nitroso compound according to claim 1, wherein the liquid to be treated is a remaining liquid obtained upon reclaiming an aqueous solution of amines used for absorbing carbon dioxide in a combustion exhaust gas.

4. The method for decomposing the nitroso compound according to claim 1, further comprising, when the liquid to be treated is basic, neutralizing the liquid to be treated using at least one selected from the group consisting of hydrochloric acid, hydrobromic acid, hydroiodic acid, sulfuric acid and nitric acid before the heating of the liquid.

5. A method for decomposing a nitroso compound in a method for recovering carbon dioxide in a gas to be treated, the method comprising:
a step (I) of bringing a gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid;
a step (II) of heating the $CO_2$ rich absorption liquid for releasing the carbon dioxide to regenerate the $CO_2$ lean absorption liquid;
a step (IIIa) of adding an aqueous solution containing hydrogen halide to part of the $CO_2$ lean absorption liquid regenerated in the step (II) that contains the nitroso compound so as to obtain a mixture, wherein an amount of the hydrogen halide in the mixture is 2 mol or more and 20 mol or less per mol of a nitroso group in the nitroso compound contained in the part of the $CO_2$ lean absorption liquid regenerated in the step (II), and subsequently heating the mixture at a temperature of not lower than 75° C. and not higher than 100° C. and under ordinary pressure to decompose the nitroso compound; and
a step (IV) of providing the step (I) with the rest of the $CO_2$ lean absorption liquid regenerated in the step (II) and/or the mixture heated in the step (Ma) to be mixed with the $CO_2$ lean absorption liquid for bringing into contact with the gas to be treated that contains carbon dioxide in the step (I).

6. A method for decomposing a nitroso compound in a method for recovering carbon dioxide in a gas to be treated, the method comprising:
a step (I) of bringing a gas to be treated that contains carbon dioxide into contact with a $CO_2$ lean absorption liquid containing amines for absorbing the carbon dioxide into the $CO_2$ lean absorption liquid to obtain a $CO_2$ rich absorption liquid;
a step (II) of heating the $CO_2$ rich absorption liquid for releasing the carbon dioxide to regenerate the $CO_2$ lean absorption liquid;
a step (V) of reclaiming a part of the $CO_2$ lean absorption liquid regenerated in the step (II) to remove a heat stable salt;
a step (IIIb) of adding an aqueous solution containing hydrogen halide to a remaining liquid obtained in the step (V) that contains the nitroso compound so as to obtain a mixture, wherein an amount of the hydrogen halide in the mixture is 2 mol or more and 20 mol or less per mol of a nitroso group in the nitroso compound contained in the remaining liquid, and subsequently heating the mixture at a temperature of not lower than 75° C. and not higher than 100° C. and under ordinary pressure to decompose the nitroso compound and recover amines; and a step (IV) of providing the step (I) with the rest of the $CO_2$ lean absorption liquid regenerated in the step (II) and/or the amines recovered in the step (IIIb) to be mixed with the $CO_2$ lean absorption liquid for bringing into contact with the gas to be treated that contains carbon dioxide in the step (I).

* * * * *